United States Patent
Smith et al.

(10) Patent No.: US 8,028,816 B1
(45) Date of Patent: Oct. 4, 2011

(54) CONTAINER HANDLING SYSTEM

(75) Inventors: Paul Smith, San Clemente, CA (US);
Michael Callahan, Valinda, CA (US);
William H. Collier, Irvine, CA (US);
Albert J. Sturm, Jr., Stillwater, MN (US)

(73) Assignee: Par Systems, Inc., Shoreview, MN (US)

( * ) Notice: Subject to any disclaimer, the term of this patent is extended or adjusted under 35 U.S.C. 154(b) by 595 days.

(21) Appl. No.: 12/020,919

(22) Filed: Jan. 28, 2008

Related U.S. Application Data

(60) Provisional application No. 60/886,769, filed on Jan. 26, 2007.

(51) Int. Cl.
*B65G 47/84* (2006.01)

(52) U.S. Cl. .................. 198/457.01; 198/394; 198/379; 53/253

(58) Field of Classification Search ......................... None
See application file for complete search history.

(56) References Cited

U.S. PATENT DOCUMENTS

| | | | | |
|---|---|---|---|---|
| 3,509,684 A | * | 5/1970 | Scribner et al. | 53/48.4 |
| 4,624,098 A | * | 11/1986 | Trendel | 53/314 |
| 5,261,207 A | * | 11/1993 | Bedin | 53/284.5 |

* cited by examiner

*Primary Examiner* — Gene Crawford
*Assistant Examiner* — Kavel Singh
(74) *Attorney, Agent, or Firm* — Steven M. Koehler; Westman, Champlin & Kelly, P.A.

(57) ABSTRACT

A bench-supported container handling system includes a bottom panel and a container manipulating device. A container conveying assembly is configured for transporting containers along a first direction while a container part conveying assembly is configured for transporting a part of the container along a second direction that intersects with the first direction. The first direction and the second direction are configured so as to create an area where the container manipulating device can be disposed. Additional aspects include a capping assembly and a labeling assembly.

27 Claims, 15 Drawing Sheets

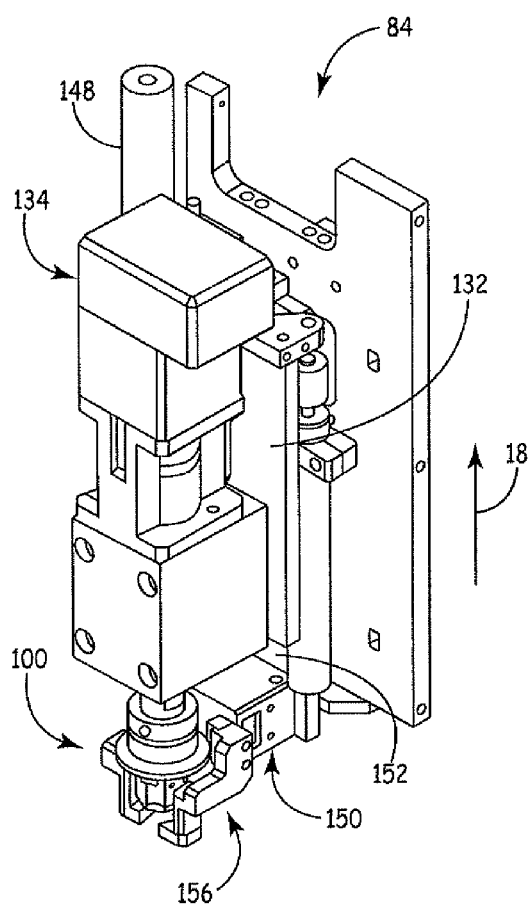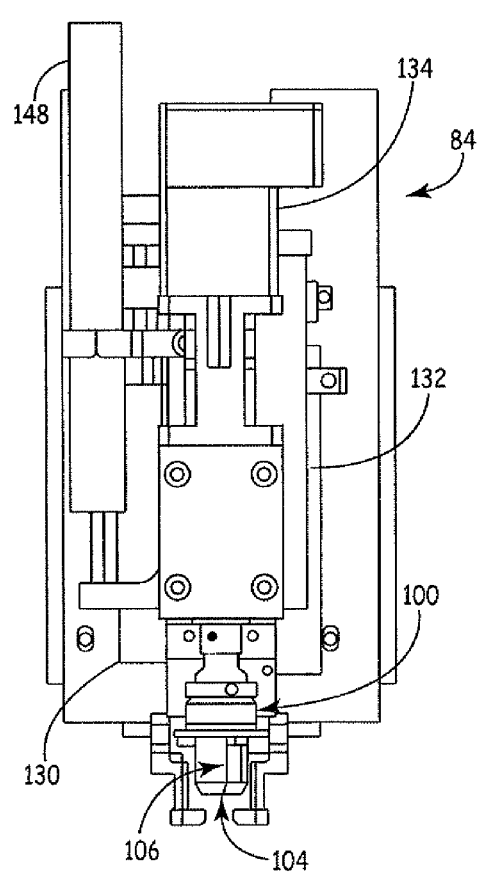
FIG. 7
FIG. 8

CONTAINER HANDLING SYSTEM

CROSS-REFERENCE TO RELATED APPLICATION

The present application is based on and claims the benefit of U.S. provisional patent application Ser. No. 60/886,769, filed Jan. 26, 2007, the content of which is hereby incorporated by reference in its entirety.

BACKGROUND

The discussion below is merely provided for general background information and is not intended to be used as an aid in determining the scope of the claimed subject matter.

In certain fields such as but not limited to laboratory facilities, a relatively large number of small containers must be processed quickly, accurately and/or efficiently. Such containers are, for example, filled with specimen samples, chemicals, reagents, or other materials, and typically comprise plastic or glass tubes or vials with caps or stoppers, which are often used to collect or prepare samples. Before or after being filled, labels are often affixed to the containers. The labels generally include a reference name or number, written information disclosing the nature of the sample or material contained in the container, and/or a bar code for easy reference to computer records of the sample or material. The information described above is printed on a pressure sensitive label for attachment to the container. Processing step(s) that must be repeated for each of the containers to name just a few can include sorting the containers, filling or unfilling the containers, applying or removing caps or stoppers and/or applying or reading each of the labels.

SUMMARY

This Summary and Abstract are provided to introduce some concepts in a simplified form that are further described below in the Detailed Description. This Summary and Abstract are not intended to identify key features or essential features of the claimed subject matter, nor are they intended to be used as an aid in determining the scope of the claimed subject matter. In addition, the description herein provided and the claimed subject matter should not be interpreted as being directed to addressing any of the short-comings discussed in the Background.

A first aspect herein described is a bench-supported container handling system includes a bottom panel and a container manipulating device. A container conveying assembly is configured for transporting containers along a first direction while a container part conveying assembly is configured for transporting a part of the container along a second direction that intersects with the first direction. The first direction and the second direction are configured so as to create an area where the container manipulating device can be disposed.

Additional aspects include a capping assembly and a labeling assembly. The capping assembly includes a gripping assembly adapted to hold a container and a cap holder assembly adapted to hold a cap. A motor is connected to the cap holder to rotate the cap.

The labeling assembly includes a gripping assembly adapted to hold a container and a labeling station. The labeling station includes two rollers adapted to rotate the container. A label transporting assembly is adapted to transport the label and includes a third roller positionable relative to the first two rollers so as to hold the container between all the rollers while a label is attached to the container.

BRIEF DESCRIPTION OF THE DRAWINGS

In the drawings:

FIG. 7 is a perspective view of a capping assembly.

FIG. 8 is a front elevational view of the capping assembly.

DETAILED DESCRIPTION OF THE ILLUSTRATIVE EMBODIMENTS

Figure 1:
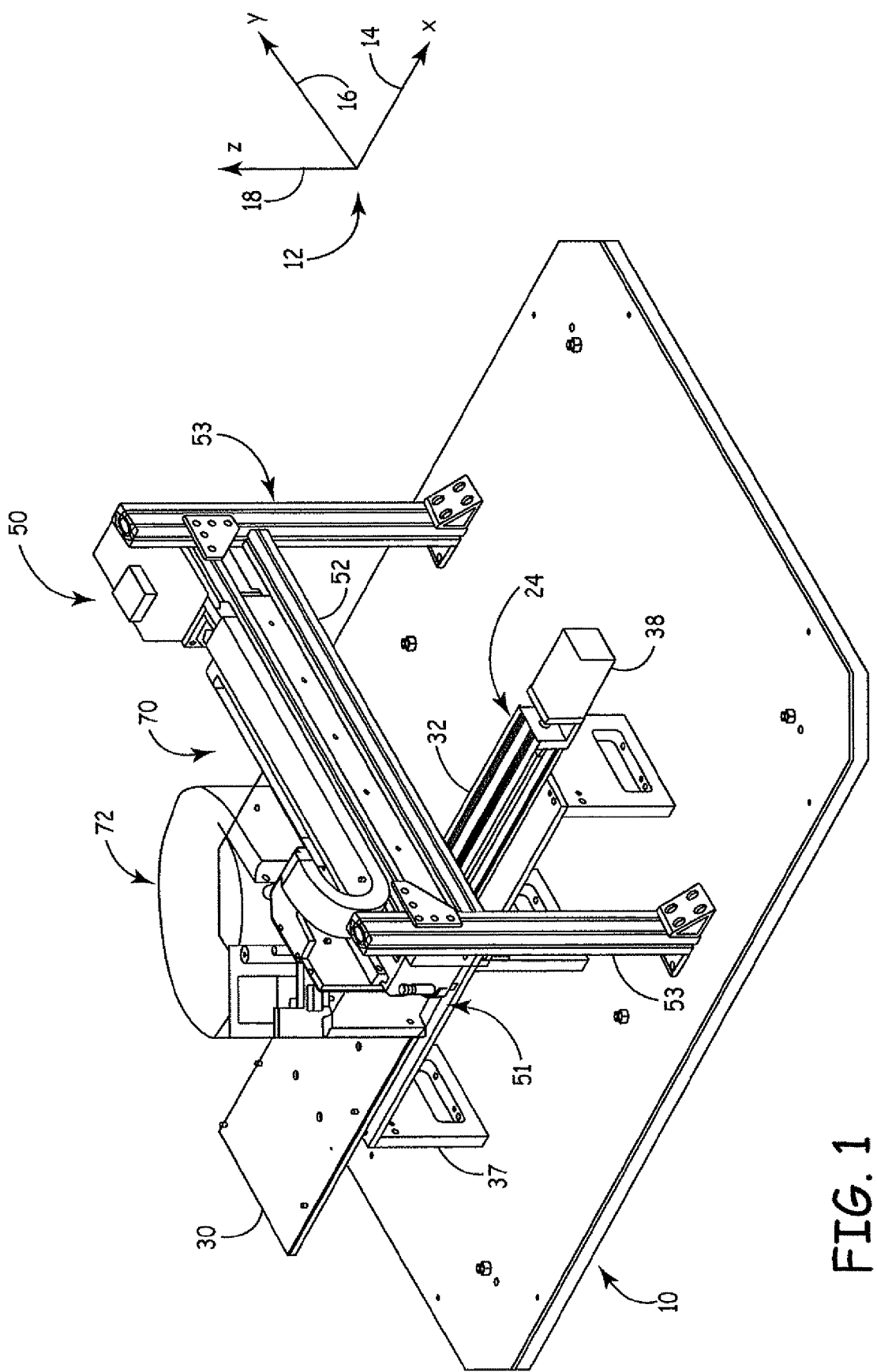
FIG. 1 is a perspective view of a bench-supported container handling system with parts removed.

FIG. 1 illustrates a multi-axis, linear motion container handling system 10 comprising an aspect of the present invention. The container handling system 10 manipulates containers (herein exemplified as comprising tubes or vials) or parts thereof, using linear motion in two or three, commonly, orthogonal degrees of motion. For purposes of explanation, a reference coordinate system indicated at 12 comprises an X-axis 14, a Y-axis 16 and a Z-axis 18 is provided.

Figure 2:
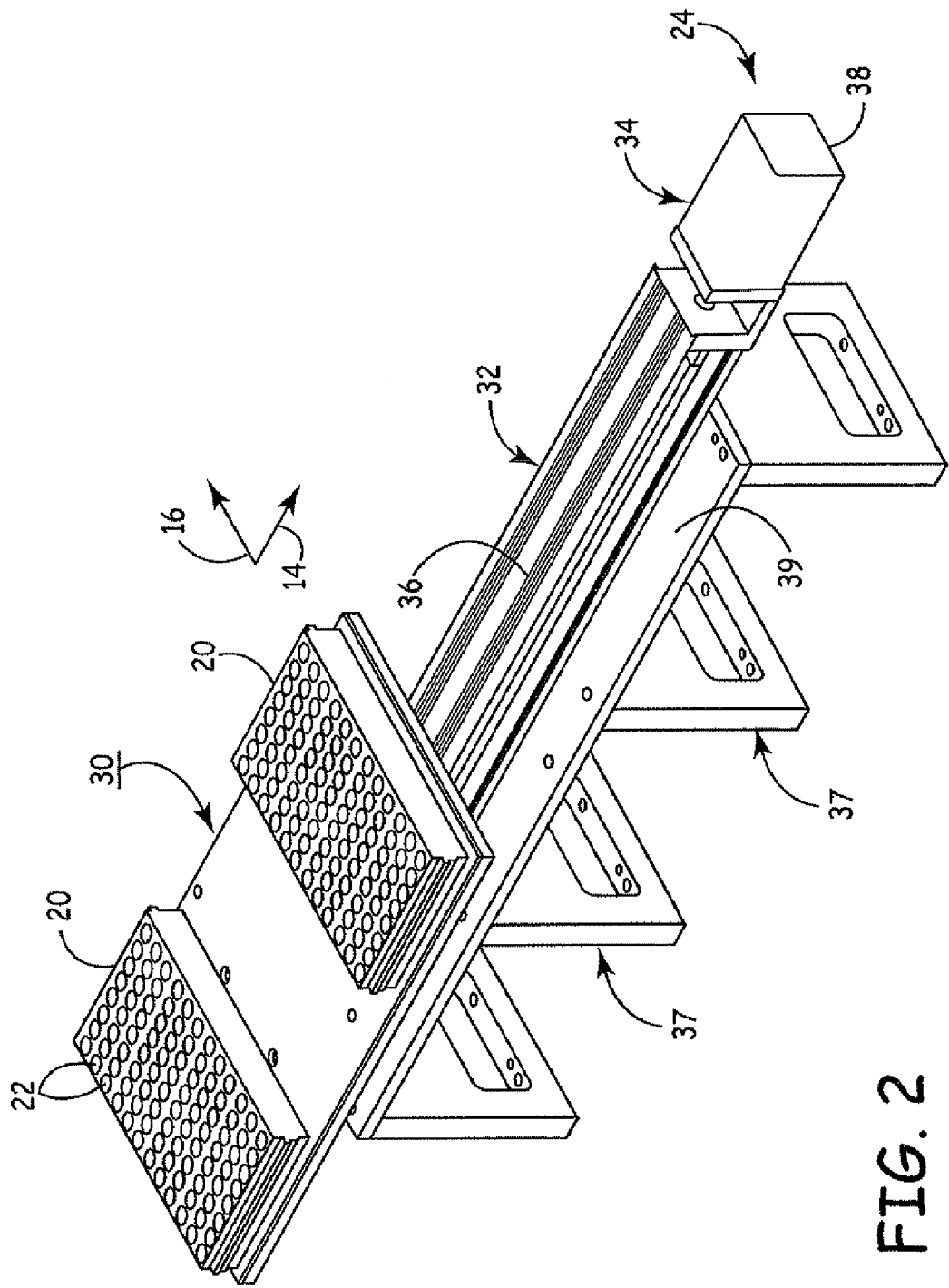
FIG. 2 is a perspective view of a tray conveying assembly.

Referring also to FIG. 2, generally, container handling system 10 is used to process each of a plurality of containers typically grouped in batches. In the exemplary embodiment, batches of containers are held in place and transported using a container holder tray 20 having separate recesses or apertures 22 of size to hold one container. The apertures 22 are commonly organized in a two-dimensional grid, herein aligned with the X-axis 14 and the Y-axis 16, although it should be understood other aperture patterns can be used.

Container handling system 10 includes a tray conveying assembly 24 configured to transport each tray 20 linearly, along the X-axis 14. Typically, movement is performed in a step-wise manner with displacements, or a series of displacements, equal to the spacing of aligned apertures 22 forming each of the rows in the direction of the Y-axis 16. In the embodiment illustrated, the tray conveying assembly 24 includes a support plate 30 configured to support one or more trays 20 each in a fixed and known position. The support plate 30 is guided along a rail 32 (oriented to be parallel to the X-axis 14) either directly sliding thereon or supported with rollers, wheels, or the like. A displacement actuator 34 selectively displaces the support plate 30 on the rail 32. Numerous mechanisms can be used to cause such displacement. One particularly advantageous and simple mechanism is an elongated threaded rod 36 oriented to be parallel to the rail 32 and supported by the rail 32 for rotation about its longitudinal axis. A nut (not shown) is fixedly coupled to the support plate 30 and threadably mates with the rod 36. The rod 36 is also coupled to a rotary actuator 38 such as an electric, pneumatic or hydraulic motor. Selective rotation of the rod 36 by the rotary actuator 38 causes corresponding linear displacement of the nut and thus the support plate 30 relative to the rod 36. Although illustrated and described using the rotary actuator 38 and rod 36, it should be understood direct operating linear actuators for displacing the support plate 30 along the rail 32 can also be used. The linear actuators can be electric, pneumatic and/or hydraulic. For example, a linear electric motor can be used, if desired. Displacement actuator 34 can be elevated as illustrated in FIG. 2 by being supported by supports 37 and mounting plate 39.

Figure 3:
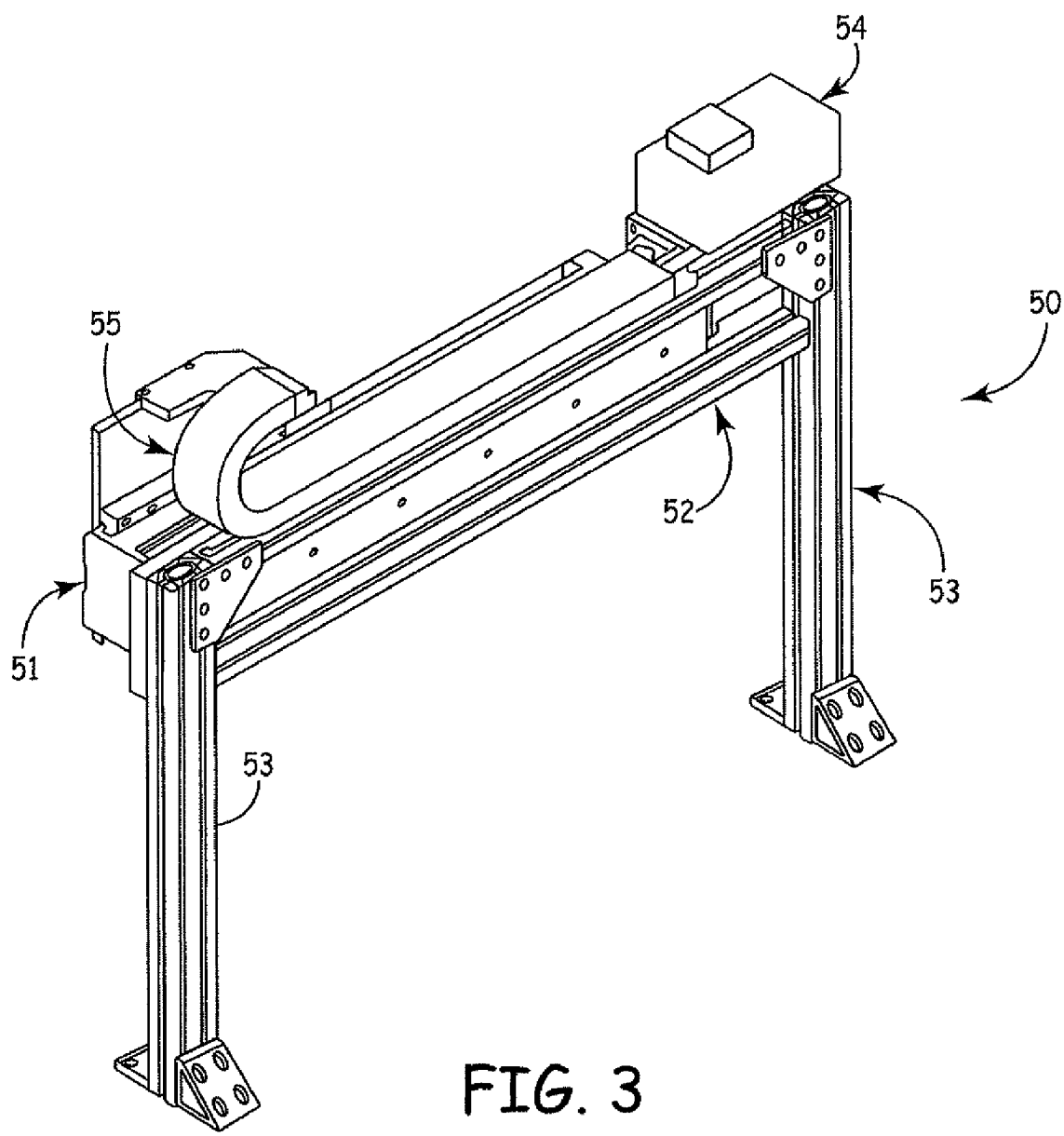
FIG. 3 is a perspective view of a container part conveying assembly.
Figure 4:
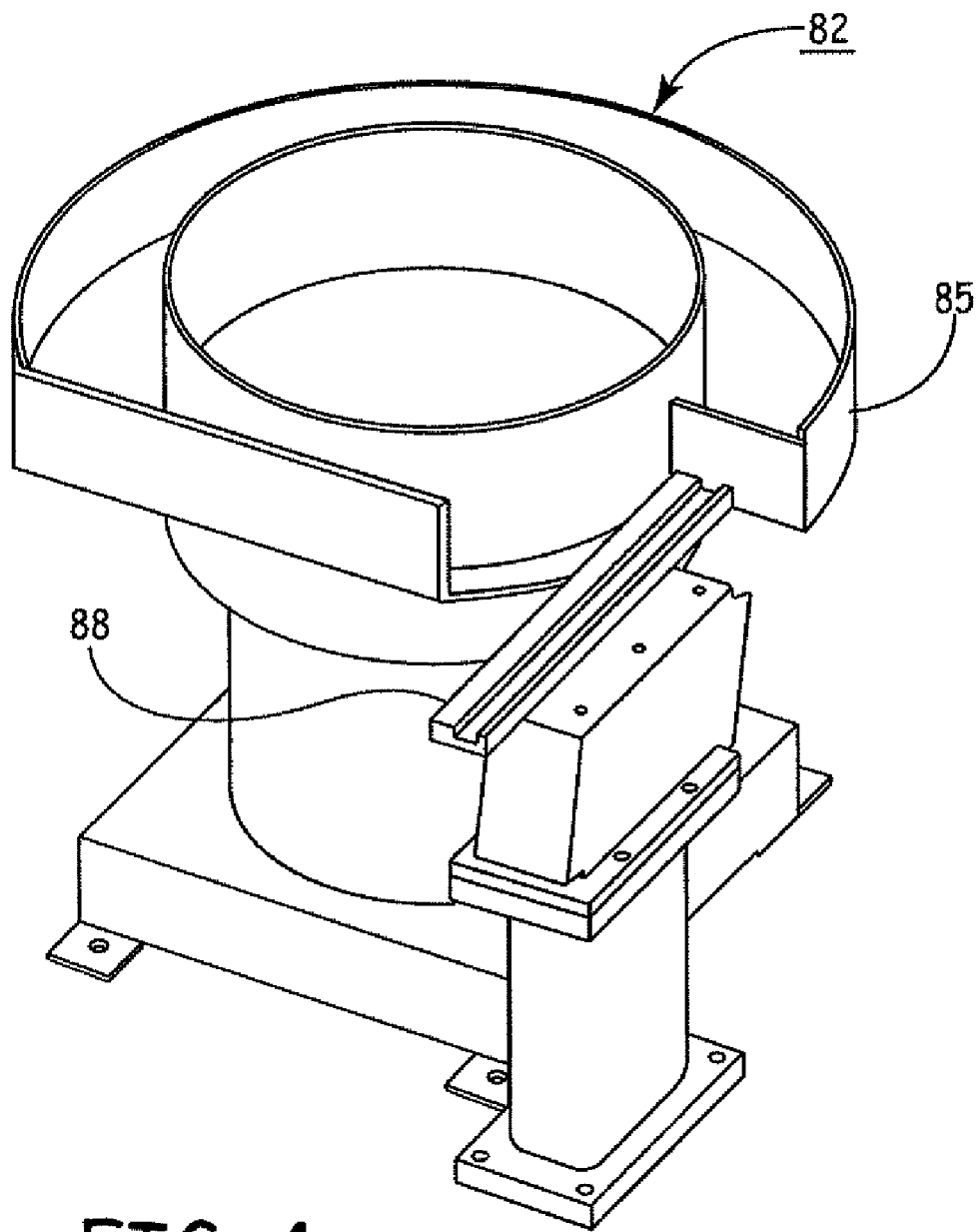
FIG. 4 is a perspective view of a cap feeder.
Figure 5:
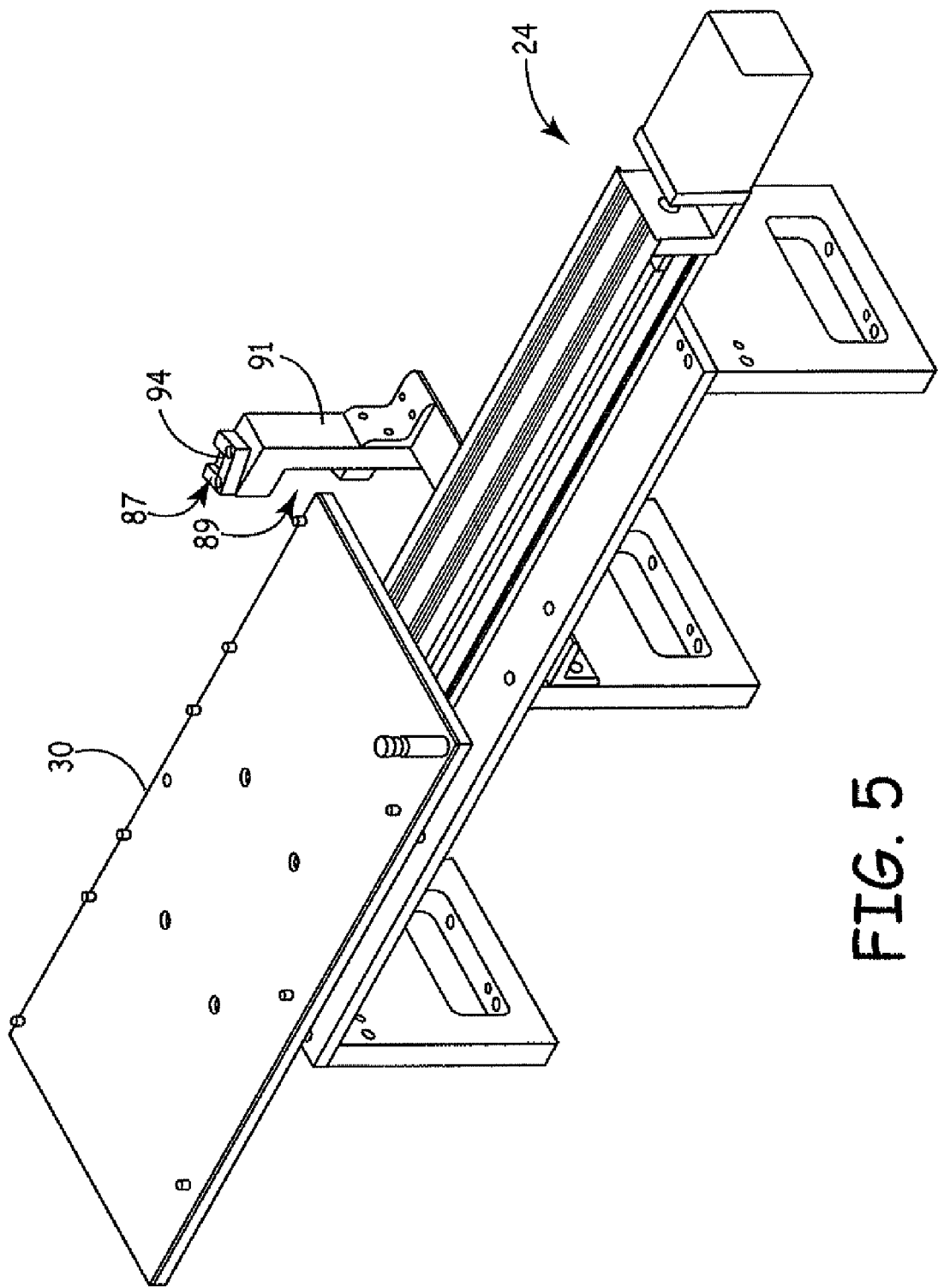
FIG. 5 is a perspective view of the container tray assembly and a cap receiver.
Figure 6:
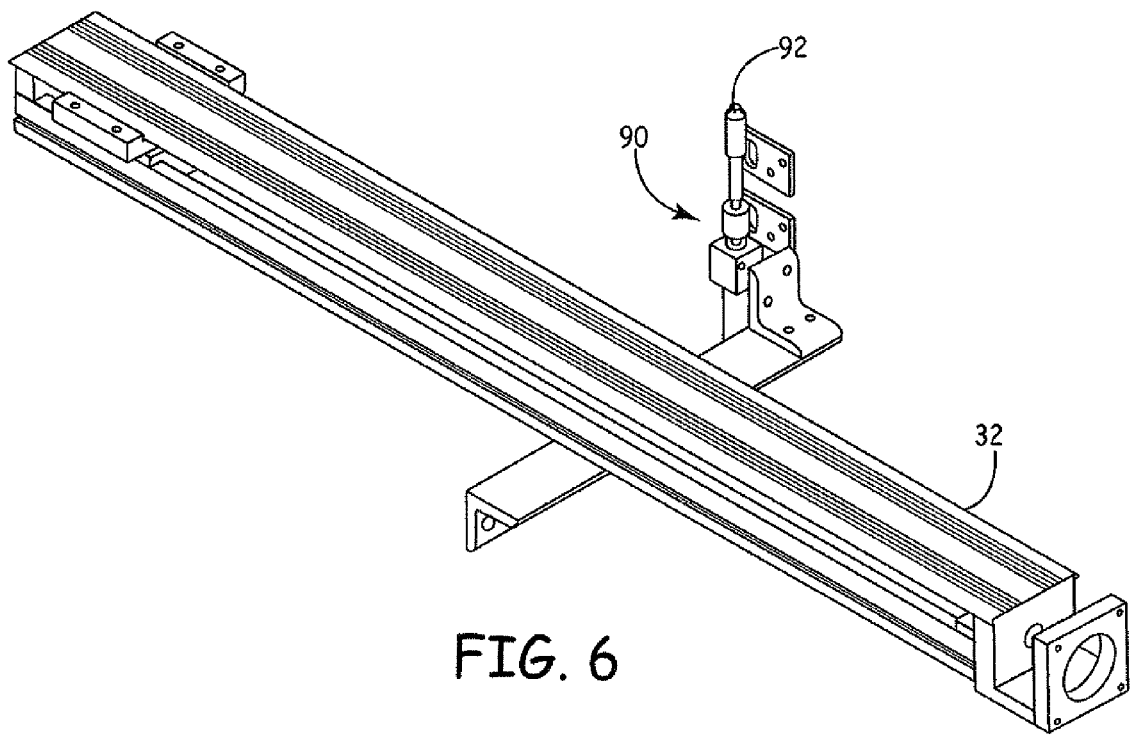
FIG. 6 is a perspective view of the container tray assembly and cap receiver with parts removed.

In the embodiment illustrated in FIGS. 1 and 3, container handling system 10 further includes a container part conveying assembly 50 that is configured to transport selectively one or more individual containers (or parts thereof) to and/or from container trays 20. Container part conveying assembly 50 is separate from tray conveying assembly 24 and transports individual container parts along a path that is obtuse or orthogonal to the path of trays 20. Container part conveying assembly 50 includes a movable head 51 that is guided along a rail 52 either directly sliding thereon or supported with rollers, wheels, or the like. Rail 52 is supported on posts 53. A displacement actuator 54 selectively displaces the movable head 51 on the rail 52. Numerous mechanisms can be used to cause such displacement including electric, pneumatic and/or hydraulic actuators. Power and/or signal lines for mechanisms joined to head 51 can be managed by flexible tube 55.

The container handling system 10 is particularly advantageous in that the tray conveying assembly 24 and the container part, conveying assembly 50 can be used with many different types of devices that handle or operate upon individual containers. In particular, orientation of the tray conveying assembly 24 and the container part conveying assembly 50 with paths of travel or operation in an obtuse or orthogonal intersecting manner creates an area 70 (FIG. 1) where a container manipulating device 72 of many different forms can be disposed. This design allows the tray conveying assembly 24 and the container part conveying assembly 50 to be standardized thereby reducing costs. In the illustrative embodiments below, a container capping system 80 and a container labeling system 170 are described. Nevertheless, it should be understood that for this aspect of the invention, these are but two examples of container manipulating devices that can be used. For instance, other container manipulating devices include but are not limited to container packaging systems, container sorting systems, label reading or scanning systems, specimen diagnostic systems, filling and/or emptying devices, etc.

Referring now to FIGS. 1, and 4-9, another aspect of the present invention includes the container capping system 80. Generally, the container capping system 80 includes a cap feeder 82, typically stationary, and a capping assembly 84 mounted to and movable with movable head 51. Cap feeder 82 (FIG. 4) is a well known device, which includes a vibratory bowl 85 configured to sequentially dispose caps in a known position 86 in a cap receiver 87 (FIG. 5), herein at the end of an extending tray 88. Cap receiver 87 is disposed above a cap lifting assembly 89 that can include an actuator 90 (FIG. 6) having a displaceable rod 92 mounted to a support 91. Cap receiver 87 includes an aperture 94 through which rod 92 can extend through in order to lift the cap away from the cap receiver 87 to a position that allows the capping assembly 84 to grab it, as will be explained below. Actuator 90 can take numerous forms such as but not limited to electric, pneumatic or hydraulic operating components.

In the illustrated embodiment, capping assembly 84 is configured to selectively obtain a cap from cap feeder 82, lower the cap upon a desired container and secure the cap on the container. Subassemblies of capping assembly 84 taken by themselves or operating together comprise further aspects of the present invention. In the exemplary embodiment, capping is provided by two motions in a direction indicated by Z-axis 18 that is typically normal to the opening of the container (or parallel to a longitudinal axis normal to a plane having the opening for the container), and a twisting motion about the Z-axis 18.

Figure 10:
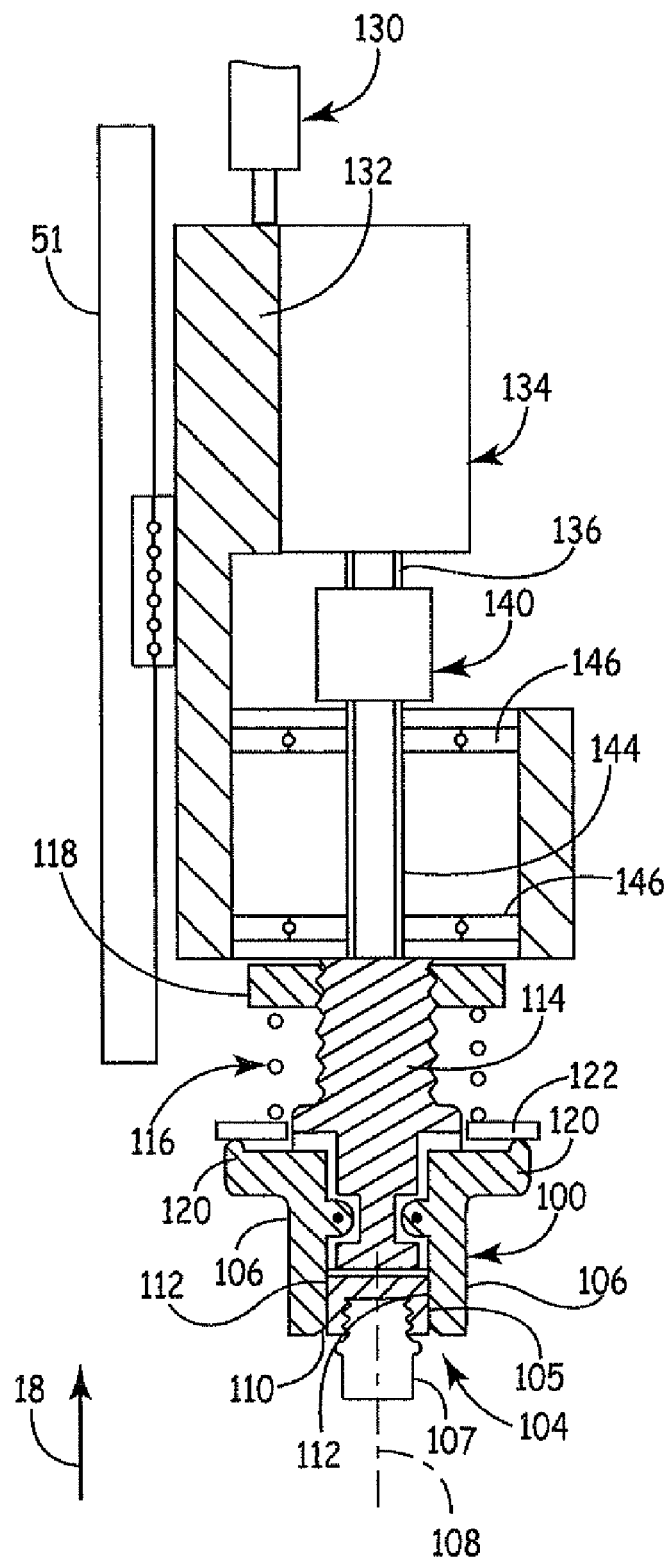
FIG. 10 is a schematic sectional view of the capping assembly.

Before container capping can occur, capping assembly first obtains a cap from cap receiver 87. Conveying assembly 50 transports the moveable head 51 with the capping assembly 84 there attached so as to position a cap holder 100 above the cap receiver 87. Referring also to FIG. 10, cap holder 100 essentially comprises a socket having a cavity, aperture or recess 104 of size to receive a cap 105. The cavity, aperture or recess 104 can be formed in many ways. In one embodiment, deflectable or movable members are used. In FIG. 10, fingers 106 engage the cap and move slightly to accommodate the cap and hold the cap with a gripping force such as provided by an actuator or, as herein described, spring force. The plurality of fingers 106 are positioned about an axis 108. Each finger 106 grips a portion of the cap 105. In the illustrated embodiment, three fingers 106 are provided and spaced at equal angular intervals about the axis 108, although the number of fingers 106 and spacing relative to each other can vary depending on the application. Each finger 106 can include a chamfered end 110 with a surface that diverges away from the axis 108 and a partially concave surface 112 adapted to engage the perimeter convex surface of the cap 105. The chamfered end 110 allows the finger 106 to deflect outwardly as the cap holder 100 receives the cap 105 since the upper edge of the cap 105 engages the chamfered end 110 and slides thereupon with relative movement of the cap 105 to the cap holder 100. The partially concave surface 112 increases the surface contact area of the finger 106 with the cap 105. The chamfered end 110 and/or concave surface 112 can be smooth and hardened, or otherwise have a texture depending for instance on the caps to be installed.

Simple deflection of the fingers 106 under spring tension can be used such as if the fingers 106 are integral with a base being formed of a single unitary body. Likewise, external springs engaging the fingers 106 can be used to increase spring tension. In yet another embodiment, the fingers 106 can move relative to the base for instance via sliding or pivoting motion under the control of a spring or actuator. In the exemplary embodiment illustrated, fingers 106 pivot on a base 114, wherein the gripping force is provided by a spring 116. Spring 116 operates in compression between a surface 118 and extending flanges 120 on each finger 106. A washer 122 distributes the spring force on each of the fingers 106 so as to be substantial equal. As the cap 105 moves relative to the fingers 106, spring 116 is compressed slightly, thereby generating a spring force tending to close the fingers 106 together via pivoting motion of each of the fingers 106 on the base 114. If desired, the spring force can be adjustable. In one embodiment as illustrated, surface 118 comprises a movable member herein illustrated as a nut threadably mating with base 114. Adjustment of the nut 118 along the base 114 changes the spring tension of spring 116. As appreciated by those skilled in the art, other forms of springs can be used. For instance, fingers 106 can be configured so as to grip the cap when one or more springs operate in tension are used.

Referring also to FIGS. 7 and 8, a first movement along the Z-axis 18 moves cap holder 100 selectively toward the desired container. In particular, an actuator 130 operably connected between the movable head 51 and a carriage 132 of the cap holder 100, slides the carriage 132 relative to the movable head 51 on suitable bearing surfaces. (It should be noted each of the actuators of capping system 84 herein mentioned can comprise electric, pneumatic or hydraulic actuators.) Carriage 132 also supports a motor 134 that is operably coupled to base 114 in order to spin the base 114, fingers 106 and thus the cap 105 on a container 107. In the exemplary embodiment, an output shaft 136 of the motor 134 is coupled to base 114 with a slip clutch 140. Slip clutch 140 is provided so as to control torque applied to the cap/container interface such that when a desired torque is obtained, the slip clutch 140 allows the output shaft 136 to turn without further tightening of the cap 105 on the container 107. An intermediate shaft 144 can be provided to join the base 114 to the slip clutch 140. Intermediate shaft 144 is supported on carriage 132 with bearing assemblies 146. Slip clutch 140 can accommodate any misalignment of the output shaft 136 with the base 114 and/or intermediate shaft 144. During twisting of the cap 105 on the container 107, there may be some movement along the Z-axis 18 due to, for example, mating threads between the cap and the container. In such situations, it may be desirable to allow the actuator 130 to "float" so as to allow limited movement of the support base 132 along of the Z-axis 18, for instance, when the cap 105 initially engages the container 107 and when the cap 105 is threaded on the container 107. A displacement sensor 148 can be provided to monitor the position of the cap holder 100. Likewise, a sensor can be provided to monitor the position of the fingers 106. However, in one embodiment, excessive operation or rotation of the motor 134 can be used to indicate that a cap was not present in the cap holder 100. It should be noted that if the cap used on the container does not threadably mate with the container, for instance where the cap slides on the container, motor 134 and other components used for twisting the cap may not be required.

Figure 9:
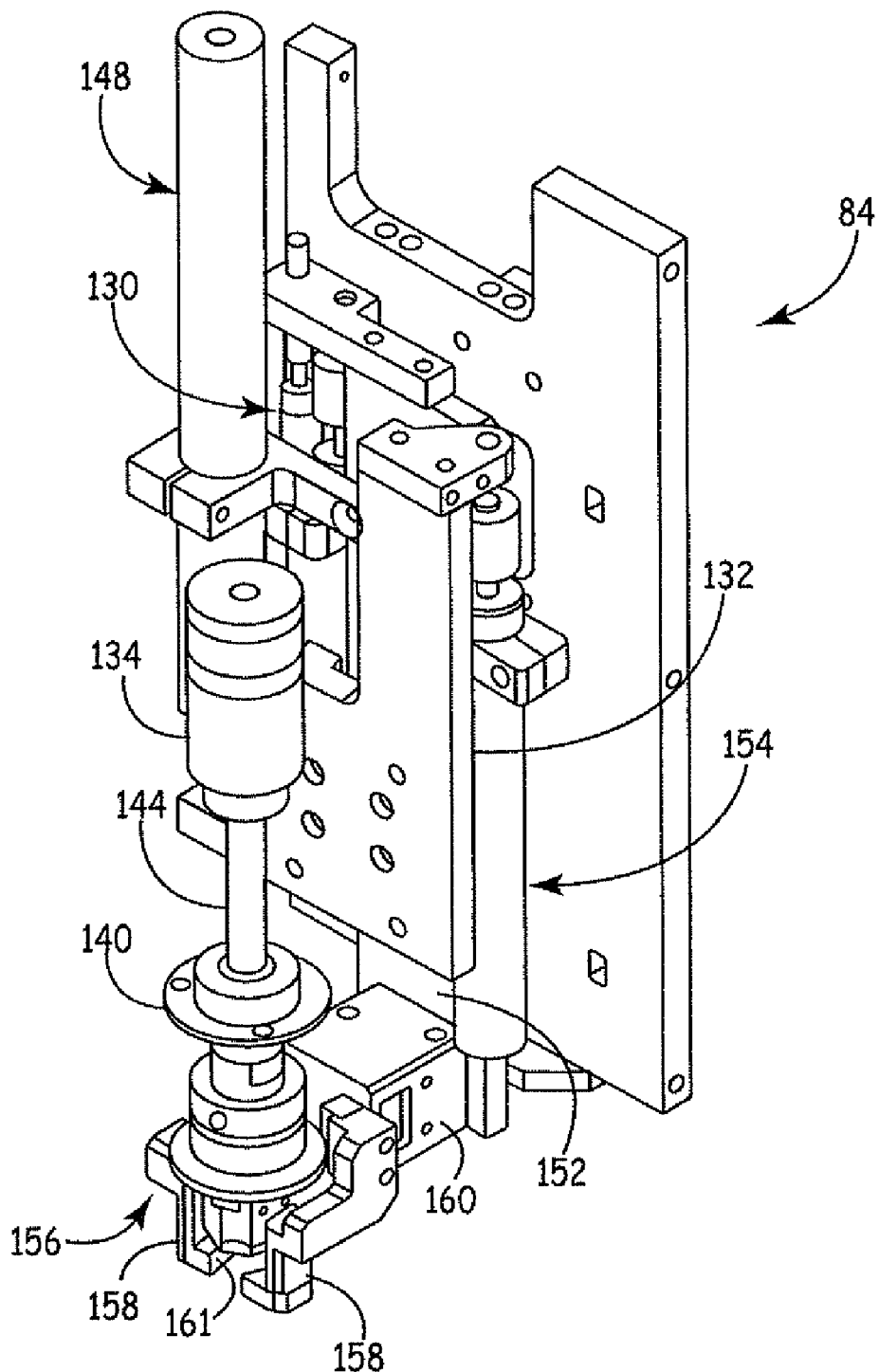
FIG. 9 is a perspective view of the capping assembly with parts removed.

Referring to FIGS. 7-9, capping assembly 84 can also include a container holder 150, which is used to hold a desired container in typically a fixed, non-rotating manner so as to allow a cap to be attached with cap holder 100. Container holder 150 also includes a carriage 152 that is mounted for movement relative to movable head 51 on suitable bearing surfaces, the movement along the Z-axis 18 of which is controlled by an actuator 154. Carriage 152 supports a gripper assembly 156. In the embodiment illustrated, gripper assembly 156 includes a plurality of grips 158. Many different types of gripper assemblies can be used. In the embodiment illustrated, at least one (herein both) of the grips 158 is operated by an actuator 160, which selectively moves the grips 158 linearly toward and away from each other. The grips 158 have concave or other suitable recesses 161 (e.g. V-shaped) so as to increase the contact surface area with the container. If desired, a displacement sensor (not shown) can be provided to monitor the position of the gripper assembly 156. Likewise, a sensor can be provided to monitor movement of the grips 158.

Operation of the capping assembly 84 as it pertains to operation of the cap holder 150 for capping and the container holder 150 for gripping the container can be performed in a multitude of different sequences. In one useful sequence, the container holder 150 is first operated to grip the container and then the cap holder 100 is operated so as to cap the container. In the embodiment described above, since the cap, is held by spring operated fingers 106, the grip is then maintained on the container while the actuator 130 is operated so as to lift the fingers 106 and release the cap therefrom.

Figure 11:
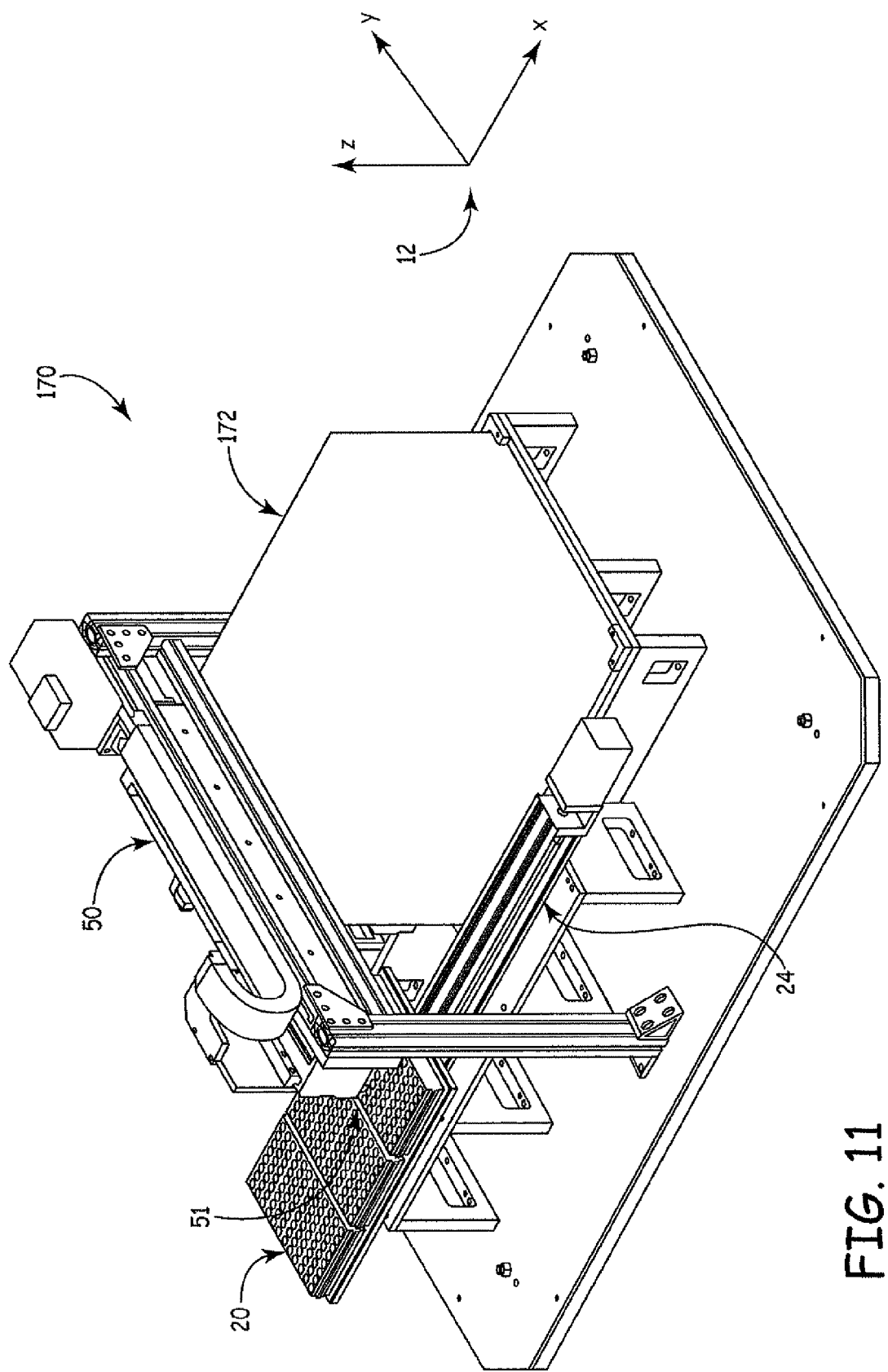
FIG. 11 is a perspective view of the container handling system with a container labeling system.
Figure 12:
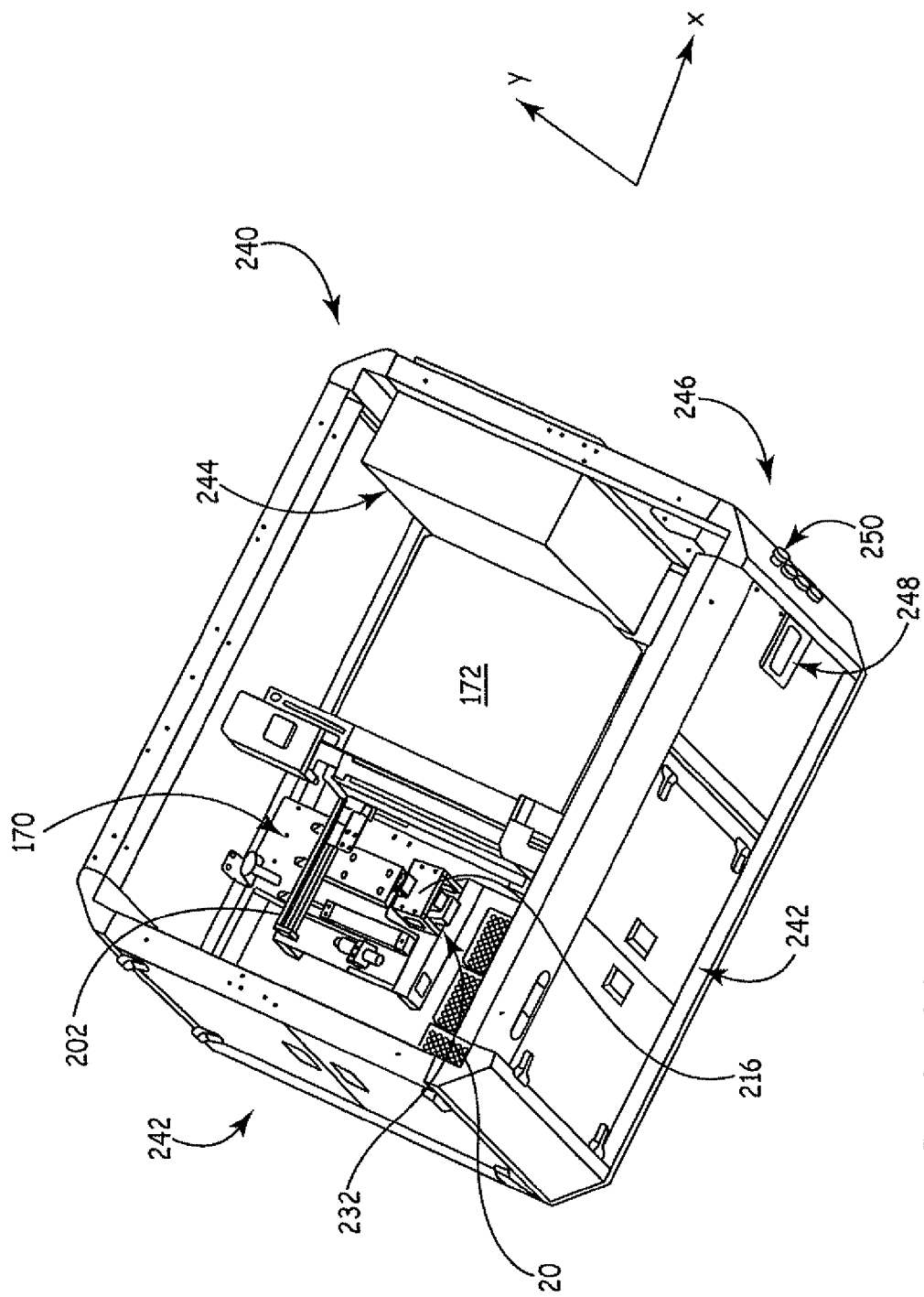
FIG. 12 is a perspective view of the container handling system in an enclosure.

FIGS. 11 and 12 generally illustrate the container labeling system 170. Tray conveying assembly 24 and container part conveying assembly 50 as described above can be provided. A suitable printer for printing labels is indicated at 172. This embodiment illustrates how the orientation and use of the tray conveying assembly 24 and container part conveying assembly 50 provides an area that can be used for different processing equipment, herein now the labeling system 170.

Figures 13, 14:
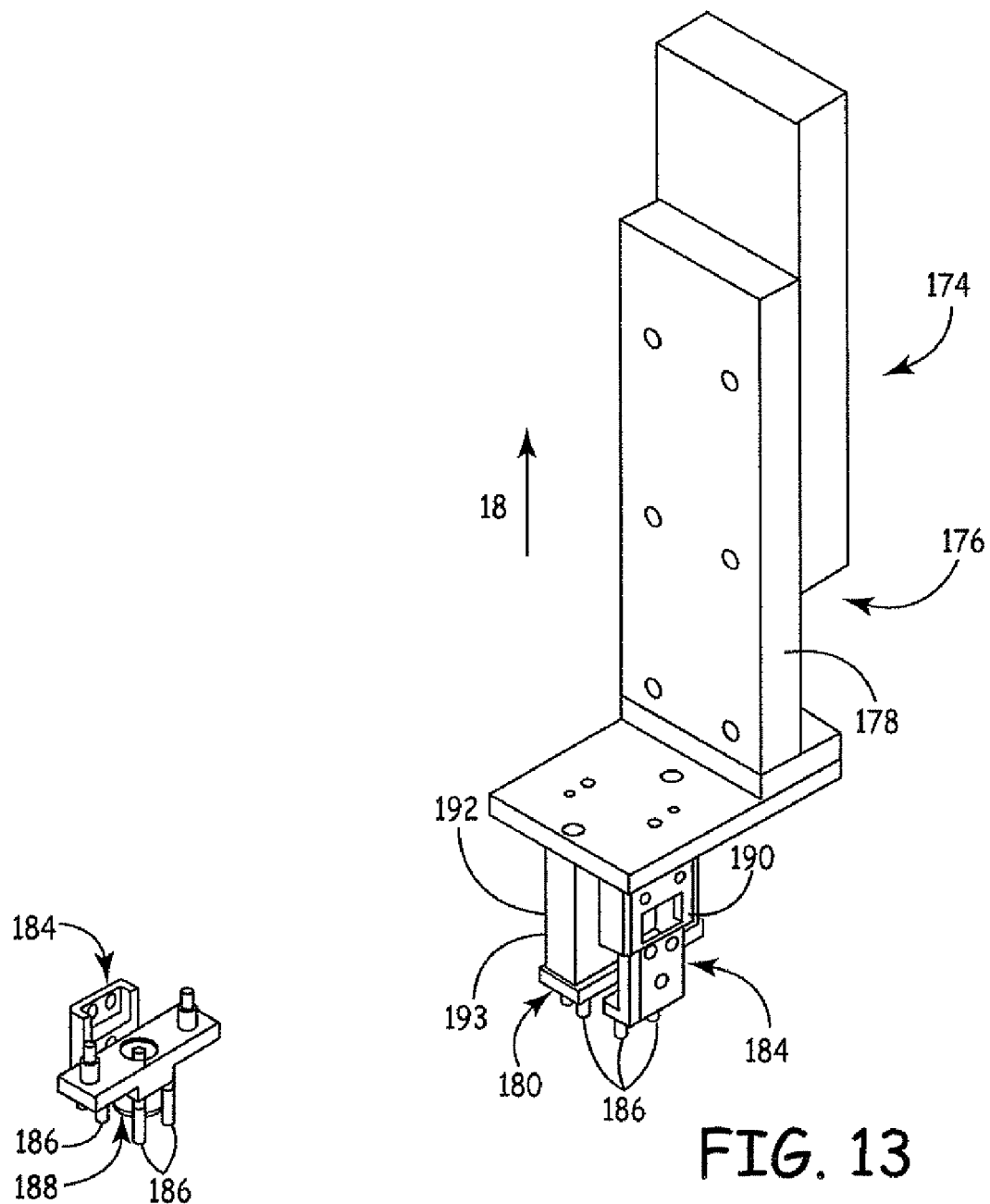
FIG. 13 is a perspective view of a container gripping assembly.
FIG. 14 is a perspective view of a portion of the container gripping assembly.

Subassemblies of labeling system 170 taken by themselves or operating together comprise further aspects of the present invention. FIGS. 13 and 14 illustrate a container gripping assembly 174 mountable to movable head 51. Container gripping assembly 174 includes an actuator slide assembly 176 configured to move a carriage 178 along the Z-axis 18 relative to movable head 51. The carriage 178 supports a gripper assembly 180 that is adapted to engage the cap on the container, transport it and if desired hold it pushing slightly down on it during labeling. The gripper assembly 180 includes opposed grips 184 (FIGS. 13 and 14), each grip having downwardly extending posts 186 to engage the cap. An actuator 190 selectively moves the grips 184 toward and away from each other. A center support assembly 192 located between the grips 184 can be provided. The center support assembly 192 can provide a slight downwardly directed force to the top of the cap through a loading mechanism such as an actuator or spring element (not specifically shown, but contained in housing 193). If desired, the center support assembly 192 can include spindle 188. The spindle 188 is configured to rotate in the direction of the tube container when the tube container is rotated typically when pressure from the grips 184 is reduced or released. Other forms of container transporting/gripping mechanisms can be used.

Figure 15:
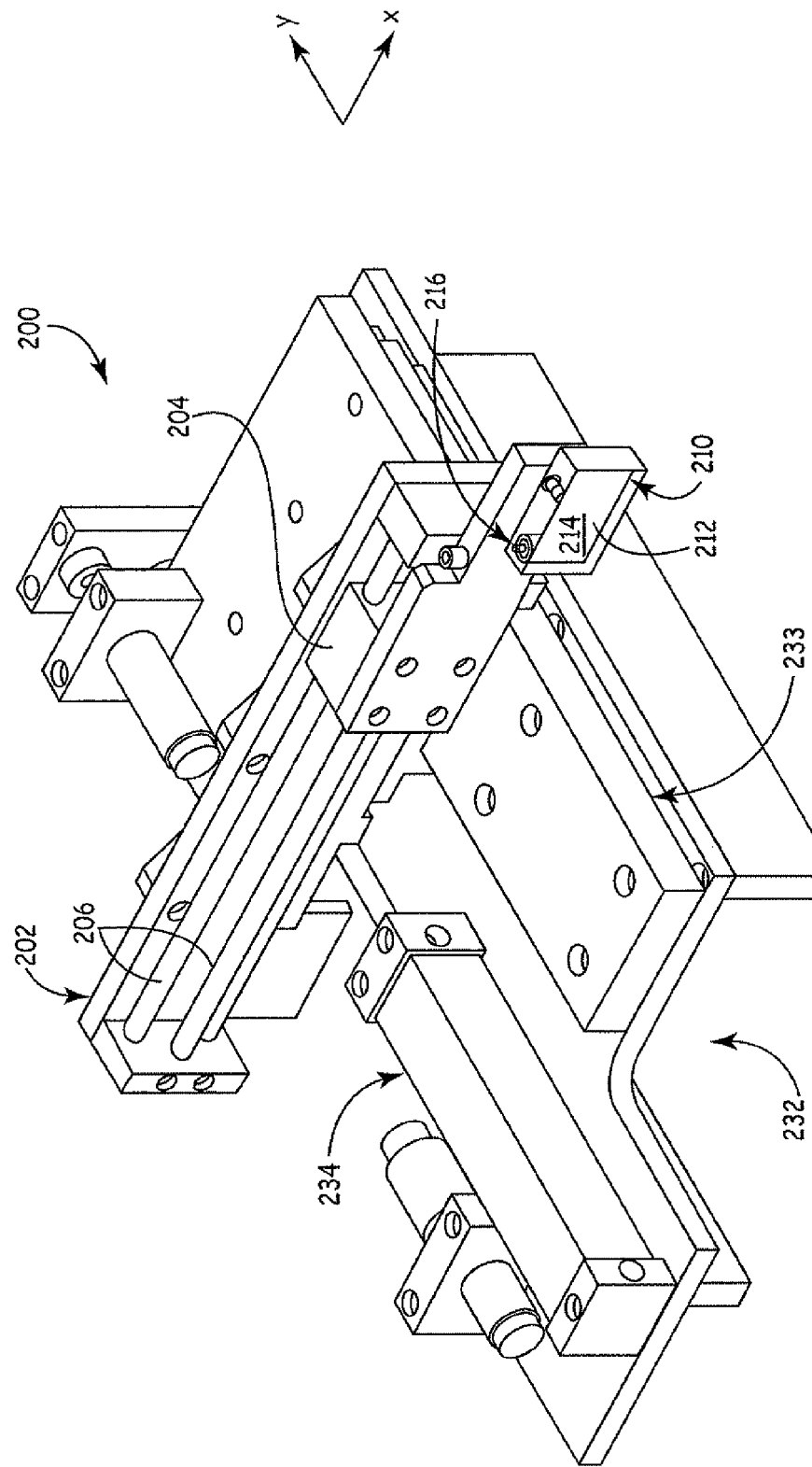
FIG. 15 is a perspective view of components of the container labeling assembly.
Figure 16:
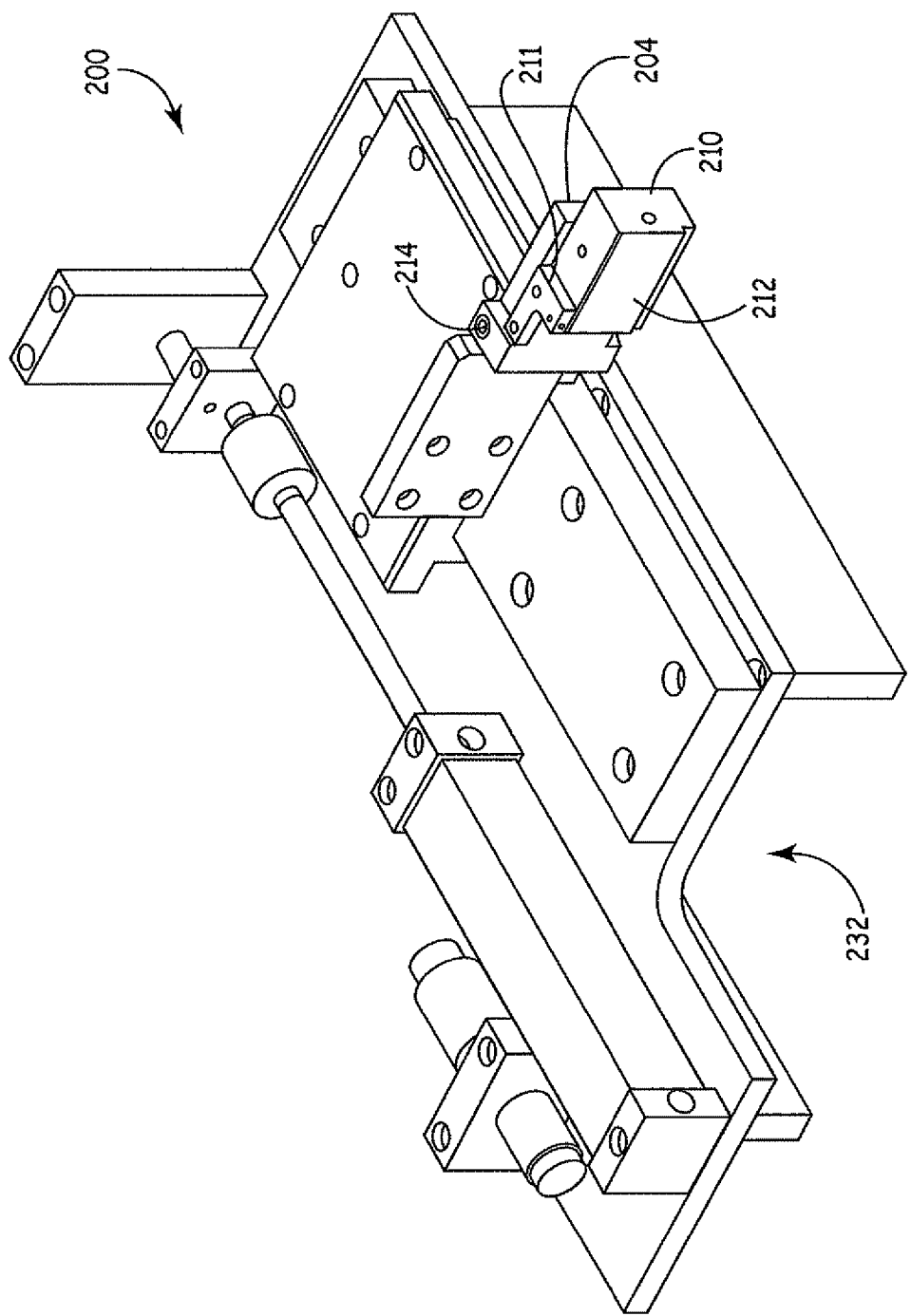
FIG. 16 is a perspective view of the components of the container labeling assembly with parts removed.

FIGS. 15 and 16 illustrate a label handling system 200 for obtaining and positioning labels. Label handling system 200 includes a slide assembly 202 having a head 204 movable on rail(s) 206, herein using an internal actuator mechanism in at least one of the rails 206, but any suitable actuator can be used. Head 204 is configured to obtain and carry a label 212 from the printer 172. In the embodiment illustrated, head 204 includes a vacuum pad 210 having apertures which use suction on the printed side of a label 212 to hold the label with the adhesive side 214 facing outwardly. Vacuum pad 210 also includes a roller 216, where an edge of the label 212 is positioned proximate to the roller 216 when obtained from the printer 172.

Referring to FIG. 16, the vacuum pad 210 is mounted to bracket 211 to pivot about a pivot pin 214 under spring tension from a suitable spring (not shown) such as a tension, compression or torsional spring that urges the vacuum pad 210 away from a back surface of the head 204.

Figure 18:
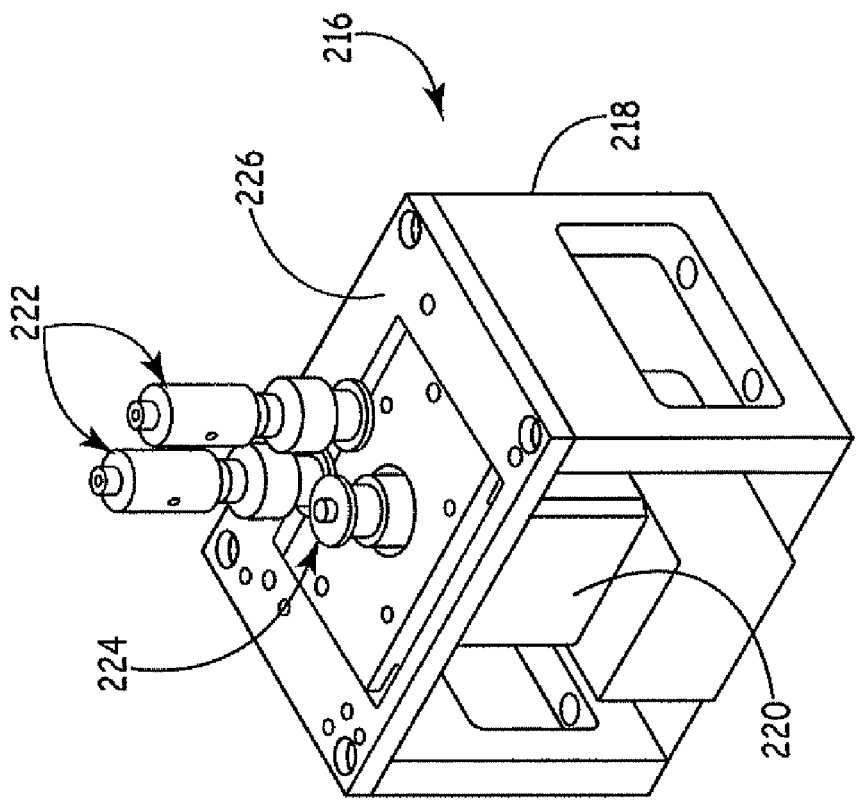
FIG. 18 is a perspective view of the labeling station with parts removed.
Figure 17:
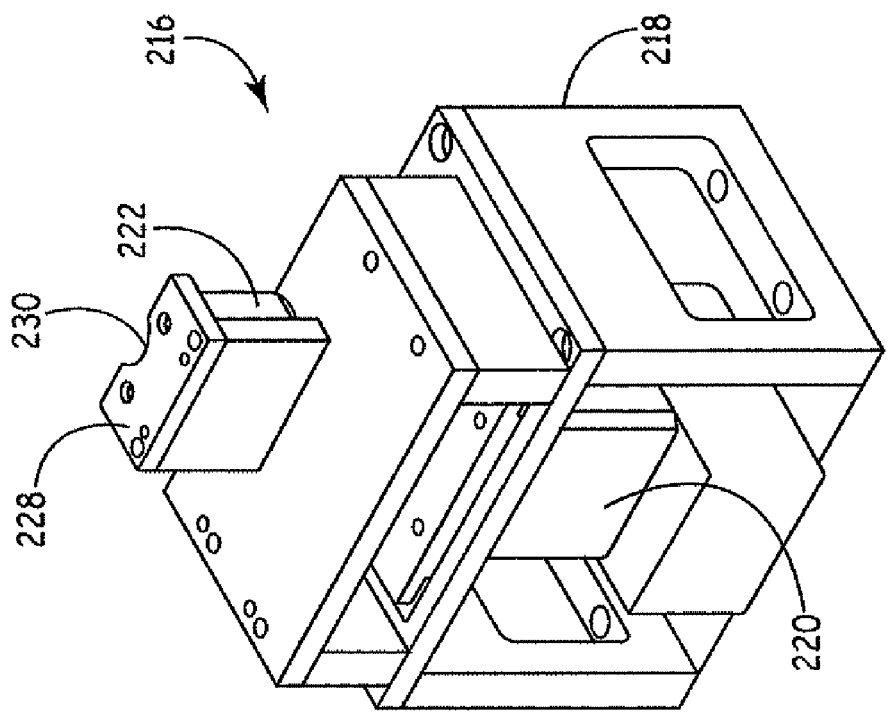
FIG. 17 is a perspective view of a labeling station.

With reference to FIGS. 17 and 18, a label applicator assembly 216 adheres the label 212 to the container, when the container part conveying system 50 moves the head 51 proximate thereto. The label applicator assembly 216 includes a frame 218 that supports a motor 220 and a pair of rollers 222. A sprocket 224 joined to the output shaft of the motor 220 is operatively connected to the rollers 222 so as to rotate the rollers 222, for example with a belt (not shown). The rollers 222 are supported on one end by a support plate 226 and by a bracket 228 at the other end. Bracket 228 includes a recess 230 so as to accommodate a container. The label applicator assembly 216 is disposed at location 232 in FIGS. 15 and 16, which is also illustrated in FIG. 12.

In operation, container part conveying system 50 transports a selected container from a tray to the label applicator assembly 216 herein using container gripping assembly 174 that flies over and then lowers the container, positioning the container proximate recess 230. With the label 212 disposed on the vacuum head 210, the vacuum head 210 is moved proximate the container with the adhesive side 214 of the label 212 contacting the container, and the roller 216 positioned between the rollers 222. In the illustrated embodiment, this movement is accomplished by movement of the head 204 on the rails 206, and movement of the slide assembly 202 on its own slide assembly 233 by an actuator 234. When the container is essentially pinched by the rollers 16, 222, motor 220 is operated to spin the container causing the label 212 to be wrapped therearound. After affixing the label 212, head 204 is moved back to the printer 172 to obtain another label and the container is returned to the tray whereat a new container is then obtained.

At this point it should be noted that elements of the capping system 84 and the labeling handling system 200 are not limited to work only with the tray conveying system 24 and container part conveying system 50 in that other forms of robots such as but not limited to multi-degree of motion articulating arms can be used.

Referring back to FIG. 12, the foregoing systems can be disposed in an enclosure 240 having side panels, top and bottom panels and access doors 242. The enclosure 240 is of size to fit in a laboratory or the like, for example, being mounted on or supported on a suitable bench or table, herein both referred to as "bench-supported." As such the enclosure and foregoing systems can be shipped as a unit. As used herein "bench-supported" means a bottom panel (or equivalent operating area for supporting and allowing operation of the components of the system) that is 30 ft$^2$ or less, and in a further embodiment 25 ft$^2$ or less. Nevertheless, separate units can be assembled in a line (where rail 32 may extend within and in between the units). Besides the foregoing systems, the enclosure can include power electronics as well as a controller represented at 244. A user interface 246 comprising a display 248 and operator switches 250 are provided on one of the side panels.

Although the subject matter has been described in language directed to specific environments, structural features and/or methodological acts, it is to be understood that the subject matter defined in the appended claims is not limited to the environments, specific features or acts described above as has been held by the courts. Rather, the environments, specific features and acts described above are disclosed as example forms of implementing the claims. In addition, workers skilled in the art will recognize that changes may be made in form and detail without departing from the spirit and scope of the inventive concepts described herein.

The invention claimed is:

1. A capping assembly comprising:
   a gripping assembly adapted to hold a container;
   a cap holder assembly adapted to hold a cap;
   a motor connected to the cap holder adapted to rotate the cap holder assembly;
   a container conveying assembly having a first rail extending in a first direction, the container conveying assembly adapted to transport a container to receive the cap;
   a container part conveying assembly having a second rail extending in a second direction and over the first rail, and wherein the container part conveying assembly comprises a head coupled to the second rail to move thereon, the head supporting the gripping assembly and the cap holder assembly.

2. The capping assembly of claim 1 wherein the gripping assembly comprises spaced apart fingers configured to hold the cap.

3. The capping assembly of claim 2 wherein the fingers are configured to deflect outwardly.

4. The capping assembly of claim 3 wherein each finger includes a chamfered end configured so as to deflect the finger outwardly with relative movement of a cap along the finger.

5. The capping assembly of claim 3 wherein each finger includes a concave surface configured to engage a cap.

6. The capping assembly of claim 5 wherein each finger is pivotally mounted to a base and further comprising a spring operably coupled to each of the fingers so as to urge the fingers together.

7. The capping assembly of claim 6 and comprising an element operably coupled to the spring to adjust a spring force used to urge the fingers together.

8. The capping assembly of claim 7 wherein the spring comprises a compression spring operably coupled to an element configured to engage a flange of each finger.

9. The capping assembly of claim 1 wherein the container part conveying assembly comprises a carriage coupled to and linearly displaceable on the head in a vertical direction, and an actuator operably coupled to the head and the carriage to displace the carriage relative to the head, the carriage supporting the cap holder assembly.

10. The capping assembly of claim 9 wherein the actuator is configured to float in the vertical direction.

11. The capping assembly of claim 1 wherein the first direction is oriented orthogonal to the second direction.

12. The capping assembly of claim 1 wherein the first direction is oriented obtuse to the second direction.

13. The capping assembly of claim 1 wherein the container conveying assembly is configured to transport a plurality of tubes each in an upright position.

14. The capping assembly of claim 1 wherein the gripping assembly includes opposed grips configured to grip a container comprising a tube, and a support disposed between the opposed grips configured to engage an upper portion of the tube allowing the tube to rotate.

15. The capping assembly of claim 14 wherein the support is configured to provide a downwardly directed force upon the upper portion of the tube.

16. The capping assembly of claim 15 wherein the support includes a rotatable spindle configured to rotate in the direction of the tube when the tube is rotated.

17. The capping assembly of claim 1 and further comprising a label handling system configured to attach labels to containers.

18. The capping assembly of claim 17 wherein the labeling assembly comprises:
   a labeling station having two rollers adapted to rotate the container; and
   a label transporting assembly adapted to transport a label, the labeling transporting assembly including a third roller positionable relative to the two rollers so as to hold the container between all of the rollers when the label is attached, the label transporting assembly including a slide assembly having a head movable on a rail, the head comprising a pad with apertures configured for creating a vacuum to hold a label on the pad when a vacuum is drawn.

19. The capping assembly of claim 18 and further comprising a fourth roller mounted to move with the pad and positioned to be proximate an edge of the label when the label is disposed on the pad.

20. The capping assembly of claim 19 wherein the pad is pivotally connected to the head.

21. The capping assembly of claim 20 wherein the head includes a spring operably coupled to the head and the pad to urge the pad away from the head.

22. The capping assembly of claim 19 and further comprising a motor to drive at least one of the rollers to rotate the container.

23. A capping assembly comprising:
a gripping assembly adapted to hold a container;
a cap holder assembly adapted to hold a cap;
a motor connected to the cap holder adapted to rotate the cap holder assembly; and
a labeling assembly comprising:
a labeling station having two rollers adapted to rotate the container; and
a label transporting assembly adapted to transport a label, the labeling transporting assembly including a third roller positionable relative to the two rollers so as to hold the container between all of the rollers when the label is attached, the label transporting assembly including a slide assembly having a head movable on a rail, the head comprising a pad with apertures configured for creating a vacuum to hold a label on the pad when a vacuum is drawn.

24. The capping assembly of claim 23 and further comprising a fourth roller mounted to move with the pad and positioned to be proximate an edge of the label when the label is disposed on the pad.

25. The capping assembly of claim 24 wherein the pad is pivotally connected to the head.

26. The capping assembly of claim 25 wherein the head includes a spring operably coupled to the head and the pad to urge the pad away from the head.

27. The capping assembly of claim 24 and further comprising a motor to drive at least one of the rollers to rotate the container.

* * * * *